United States Patent [19]

Sommer et al.

[11] Patent Number: 4,543,335

[45] Date of Patent: Sep. 24, 1985

[54] DEVICE AND METHOD FOR THE QUANTITATIVE DETERMINATION OF HEPARIN IN MAMMALIAN BLOOD PLASMA

[75] Inventors: Ronald G. Sommer; Alfred C. Greenquist, both of Elkhart, Ind.

[73] Assignee: Miles Laboratories, Inc., Elkhart, Ind.

[21] Appl. No.: 450,984

[22] Filed: Dec. 20, 1982

[51] Int. Cl.$^4$ .......................................... G01N 33/48
[52] U.S. Cl. ......................................... 436/69; 422/56; 435/13; 436/169; 436/170; 427/2
[58] Field of Search ............... 356/445, 446, 317, 318, 356/417; 422/56, 57, 60, 61; 427/2; 435/13, 805; 436/69, 166, 169, 170

[56] References Cited

U.S. PATENT DOCUMENTS

| | | |
|---|---|---|
| Re. 30,267 | 5/1980 | Bruschi .............................. 422/56 X |
| 3,891,507 | 6/1975 | Breuer ................................ 422/56 X |
| 4,181,500 | 1/1980 | Cowsar et al. ..................... 422/56 X |
| 4,234,682 | 11/1980 | Bartl et al. ......................... 436/94 X |
| 4,390,343 | 6/1983 | Walter ................................ 422/56 X |
| 4,442,204 | 4/1984 | Greenquist et al. .............. 422/56 X |

OTHER PUBLICATIONS

Larsen, et al., *Thrombosis Research*, vol. 13, No. 2, pp. 285-288.

*Primary Examiner*—Barry S. Richman
*Assistant Examiner*—Michael S. Gzybowski
*Attorney, Agent, or Firm*—Roger N. Coe; Jerome L. Jeffers

[57] ABSTRACT

A device for the quantitative determination of heparin in mammalian blood plasma, a method for the preparation of such device and a method for determining the plasma's heparin concentration using the device. The device, which is prepared using a freeze-drying technique, comprises a first upper layer of a carrier matrix material containing a buffer, AT-III and thrombin and a second, lower layer of a carrier matrix containing a thrombin sensitive fluorogenic or chromogenic substrate being capable of interacting with thrombin in such a manner that a time-related chemical change detectable by fluorometric or spectrophotometric means takes place when thrombin and the substrate are contacted in a suitable liquid environment.

15 Claims, 2 Drawing Figures

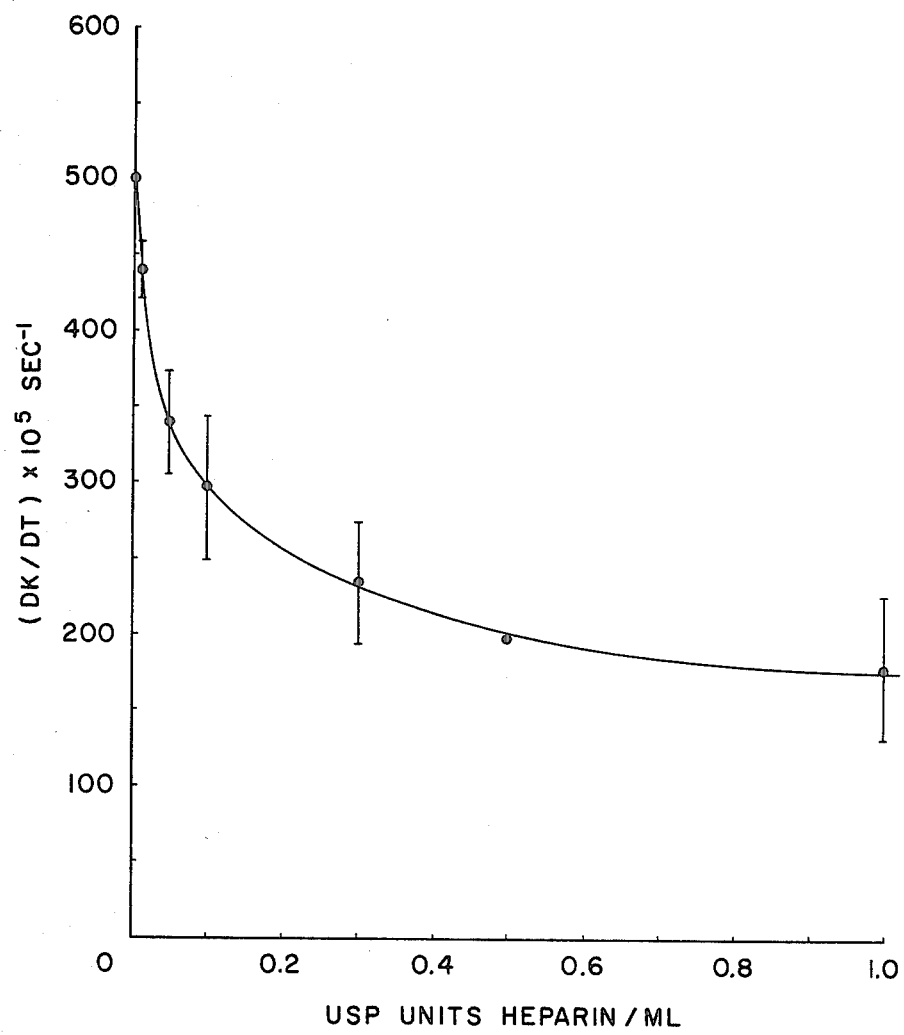
FIG. I

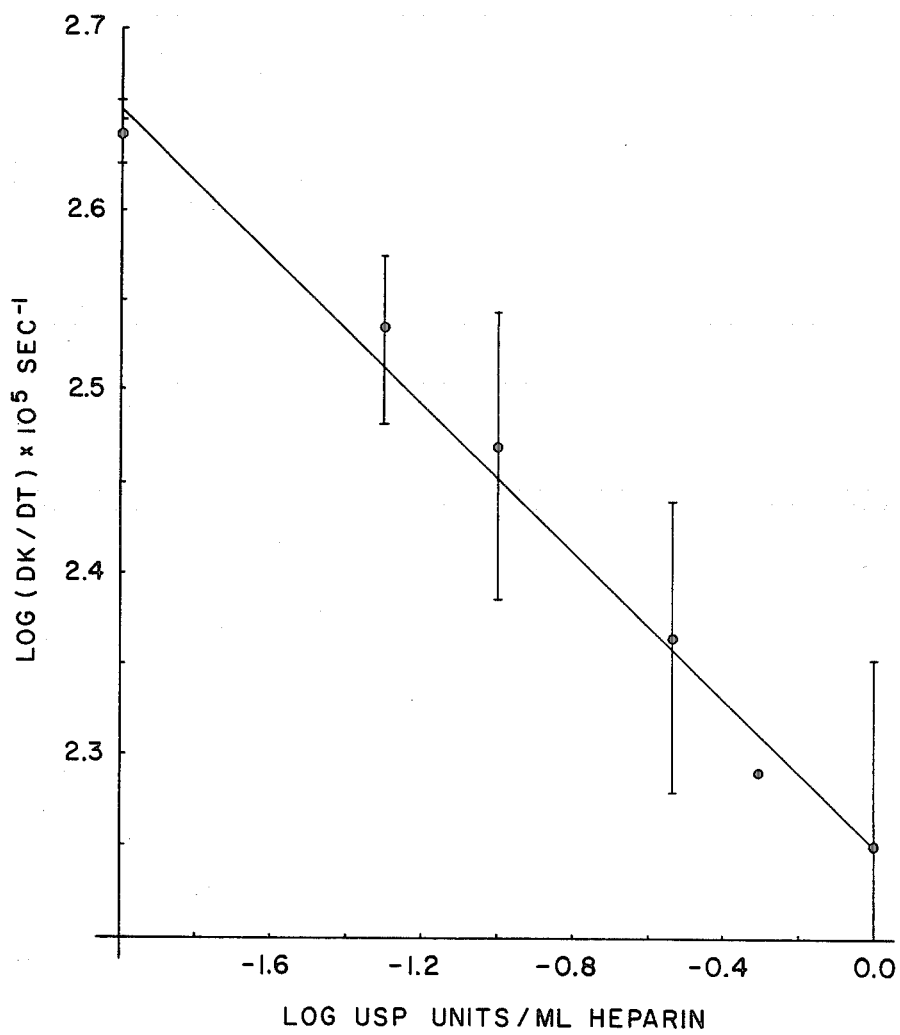
FIG. II

DEVICE AND METHOD FOR THE QUANTITATIVE DETERMINATION OF HEPARIN IN MAMMALIAN BLOOD PLASMA

BACKGROUND OF THE INVENTION

Many patients undergoing major surgery run the risk of developing postoperative thrombosis, the formation of a blood clot, that can cause death. Heparin is a powerful anticoagulant which can prevent the formation of such a life threatening clot. However, the amount of heparin in the blood must be tightly controlled so that the patient does not bleed excessively. Heparin therapy has become particularly important with the advent of major new surgical techniques such as open heart surgery and organ transplantation. Heparin is also used in some cases to treat pulmonary embolism and myocardial infraction. Because of the increasing importance of heparin therapy to control the clotting of blood and the need for careful control of heparin levels, quantitative tests for heparin in blood plasma have been developed.

Several researchers have used chromogenic or fluorogenic peptide substrates to develop quantitative tests for heparin in plasma or serum. These tests are solution tests, for example, that described by Larsen, et al in *Thrombosis Research*, Vol. 13, No. 2, pages 285–288. They are based on the measurement of free thrombin activity by the rate with which it hydrolyzes the substrate. In the measurement, advantage is taken of the reaction sequence shown in (1).

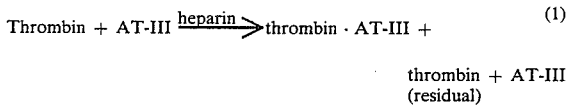

$$\text{Thrombin} + \text{AT-III} \xrightarrow{\text{heparin}} \text{thrombin} \cdot \text{AT-III} + \text{thrombin} + \text{AT-III (residual)} \quad (1)$$

Thrombin and antithrombin III (AT-III) are allowed to react for a timed period in the presence of a limiting amount of heparin. The thrombin.AT-III complex forms slowly in the absence of heparin, but very rapidly in the presence of a catalytic amount of heparin. The thrombin.AT-III complex is inactive. A thrombin sensitive substrate solution is then added, and the residual thrombin activity is measured.

This type of solution test, while an improvement over previous methods which involve timing the coagulation of whole blood samples, is still time consuming and requires the consecutive addition of several reagents. A test strip for the quantitative determination of heparin in plasma would be desirable. However, the fabrication of such a strip is problematical for two reasons. First of all, the formation of the thrombin.AT-III complex takes place very slowly, even when a catalytic amount of heparin is available, in the presence of many amidolytic substrates for thrombin. This problem can be solved by the use of a double-layered reagent strip in which the upper layer contains AT-III and thrombin and the lower layer contains the substrate. With this configuration, the interference by the substrate with the formation of the thrombin.AT-III complex can be alleviated because the complex will have already formed to an appreciable extent by the time the substrate diffuses into the upper layer upon being contacted with the plasma being tested. The second difficulty relates to the fact that thrombin and AT-III will form a complex even in the absence of heparin. Although this uncatalyzed reaction takes place slowly, the normal method of preparing the test strip by impregnating the strip with a solution of the active material (thrombin and AT-III in this case) and evaporating the water results in the formation of the thrombin.AT-III complex during preparation and storage of the test strip. For example, it was discovered that preparation of a thrombin and AT-III dip solution at room temperature, impregnation of the carrier matrix at room temperature and drying the impregnated carrier at 50° C. in a forced air oven resulted in the inhibition of 70% of the thrombin when compared with a control which contained no AT-III.

The present invention provides a method for the preparation of a test strip for the quantitative determination of heparin in blood plasma which avoids both of the difficulties discussed above.

SUMMARY OF THE INVENTION

The present invention is a method for the preparation of a device for the quantitative determination of heparin in mammalian blood plasma. The method comprises the steps of:
(a) providing a first strip of a carrier matrix material having absorbed therein a thrombin sensitive fluorogenic or chromogenic substrate and a buffer said substrate being capable of interacting with thrombin in such a manner that a time related chemical change detectable by fluorometric or spectrophotometric means takes place when thrombin and the substrate are contacted in a suitable liquid environment;
(b) contacting a second strip of a carrier matrix material with a fresh, aqueous solution containing a buffer, AT-III, and thrombin, which solution has been maintained at a temperature below about 20° C. since before the addition of the thrombin thereto to saturate the strip with the solution;
(c) removing the second strip from the solution, quick freezing it, and eliminating the solvent by freeze-drying to provide a second strip containing buffer, AT-III and thrombin;
(d) attaching the first strip to a strip of water impermeable material; and
(e) attaching the second strip to the exposed side of the first strip to form a 3-layered device suitable for the intended purpose.

Also included within the scope of this invention is the device prepared by the method set out above and the use of this device for the quantitative determination of heparin in a plasma sample.

DESCRIPTION OF THE INVENTION

The adaptation of solution technology for the assay of heparin using synthetic fluorogenic or chromogenic substrates to paper reagent strips is complicated by the necessity for a timed sequential introduction of reagents. The use of a 2-layered strip system, in order to be successful, must take into account the fact that two essential reagents, thrombin and AT-III, must be combined in one of the layers in such a manner that they do not react one with the other to form a complex either during preparation of the thrombin.AT-III containing layer or during its storage. By constructing a double-layered reagent strip with the bottom layer containing substrate and the top layer containing thrombin and AT-III and preparing the top layer in such a manner that the thrombin and AT-III do not react with each other to form a nonreactive complex, the aforementioned problems can be dealt with. By applying the thrombin and AT-III to the reagent strip top layer from a solution which has been freshly prepared and maintained at a temperature below about 20° C., (preferably below 5° C.) any reaction between the active constituents can be minimized. Since any reaction between the thrombin and AT-III is undesirable, the immediate application upon preparing the solution and the maintenance of such solution at a temperature just above its freezing point during preparation and application to the carrier matrix is suggested. The upper layer of the device needs to contain residual thrombin after its use in the heparin assay. In order to ensure the presence of residual thrombin, the ratio of thrombin to AT-III in this dip solution should be greater than 0.05 NIH unit thrombin:1 μg AT-III and preferably in the range of from 0.2 NIH unit thrombin:1 μg AT-III to 0.5 NIH unit thrombin:1 μg AT-III. Upon removal of the now saturated carrier matrix from the solution, immediate freezing and subsequent freeze-drying is desirable in order to prevent any further reaction. Freeze-drying is carried out by placing the frozen material in an apparatus in which the pressure can be reduced to a level where the evaporation of the solvent extracts sufficient heat from the material to keep it frozen. Alternatively, refrigeration of the shelf in the reduced pressure drying apparatus can keep the material below its freezing point until all the water is evaporated and the material is dry. Any combination of refrigeration temperatures and pressure which are able to maintain the material in the frozen state during the drying process is permissible. The preferred shelf temperature is −20° C. and the preferred reduced pressure is below 1 millimeter of mercury.

By constructing a double-layered reagent strip with the top layer prepared as described above and attaching it to a bottom layer containing a thrombin sensitive fluorogenic or chromogenic substrate and a buffer, the reaction between thrombin and AT-III in the top layer has an opportunity to proceed to an appreciable extent upon the application of plasma containing heparin to the top layer before diffusion of the substrate from the lower layer becomes significant enough to cause inhibition of this complex formation. There should be a water impermeable material beneath the lower layer so that sample solution does not flow onto the table of the measuring instrument and to ensure that diffusion of the substrate into the top layer will take place.

The upper layer of the testing device comprises a strip of carrier matrix material having uncomplexed thrombin and AT-III absorbed therein by the process previously described. The carrier matrix should be of a material which is capable of absorbing the blood plasma while allowing a portion of it to flow through into the bottom layer. The bottom layer which can be of the same carrier matrix material, has the substrate absorbed therein and functions by allowing the plasma fluid to solubilize the substrate thereby permitting it to flow from the bottom layer into the upper layer after the thrombin.AT-III complex has formed. This complex formation will take place rapidly upon contacting the upper layer with blood plasma because of the catalytic affect of the heparin contained therein.

Materials commonly used in the fabrication of diagnostic test strips are suitable for use as the carrier matrix. Such materials include films formed of gelatin or agarose. Typically, a bibulous material such as, for example, paper, cellulose, wood, synthetic resin fleeces, woven and nonwoven fabrics and the like is used to form the carrier matrix.

The carrier matrix can be soaked, immersed in, sprayed or printed with a fluorogenic or chromogenic substrate solution containing a buffer and dried by suitable means, such as ambient or forced air drying to leave the dry substrate/matrix combination. When the carrier is of a bibulous material, this will leave the reagent absorbed in the carrier matrix. The buffer is necessary because the rate of the thrombin enzymatic reaction is pH dependent. The pH of the buffer in both layers of the test device is designed at maximizing the reaction of thrombin and the substrate. When the substrate is S-2238, the maximum amidolytic response of thrombin is achieved at pH 8.0 to 8.5. Suitable buffers include tris (hydroxymethyl)-aminomethane (TRIS); N,N-bis-(2-hydroxymethyl)glycine and tris(hydroxymethyl)methyl aminopropanesulfonic acid. A buffer which can be the same or different from that used in preparing the substrate containing bottom layer is used in the solution from which the thrombin and AT-III is applied to the top layer. The bottom layer is prepared from a solution typically containing about 5 millimoles of substrate per liter in a buffered water solution.

Suitable chromogenic and fluorogenic substrates, their trade names where applicable, formula and detection method are set out in Table I. The abbreviations for the amino acids used in this table conform to those used by A. L. Lehninger in *Biochemistry*, Worth Publishers, Inc., New York, NY (1970) on page 67 except for pip which stands for pipecolinic acid.

TABLE I

| Trade Name/Source | Formula* | Detection Method |
|---|---|---|
| S-2160 A.B. KABi | Bz—phe—ala—arg—pNA | Absorbance at 405 nm |
| S-2238 A.B. KABi | H—D—phe—pip—arg—pNA | Absorbance at 405 nm |
| Chromozym ® TH Pentapharm LTD | Tos—gly—pro—arg—pNA | Absorbance at 405 nm |
| Abbott Qualtichrome Abbott Laboratories | $CH_3$—gly—pro—arg—pNA | Absorbance at 405 nm |
| No trade name Enzyme Systems Products | CBZ—gly—pro—arg—4MNA | Fluorescence & Absorbance Excitation-360 nm; Emission 420 nm. Absorbance at 525 nm after coupling with Fast Blue B |
| No trade name Enzyme Systems Products | H—D—phe—pro—arg—AIE | Fluorescence Excitation -335 nm; Emission-438 nm |
| No trade name Enzyme Systems Products | H—D—phe—pro—arg—4MNA | Fluorescence & Absorbance Excitation-360 nm; Emission-420 nm. Absorbance at 525 nm after |

TABLE I-continued

| Trade Name/Source | Formula* | Detection Method |
|---|---|---|
| No trade name | H—D—phe—pro—arg—AFC | coupling with Fast Blue B Fluorescence & Absorbance Excitation-400 nm; |
| Enzyme Systems Products | | Emission-505 nm. |
| No trade name | BOC—Val—pro—arg—MCA | Absorbance at 380 nm Fluorescence Excitation-380 nm; |
| Peptide Institute, Japan | | Emission-460 nm |

*The abbreviated chromophores & fluorophores are as follows:
pNA — p-nitroaniline
4MNA — 4-methoxy-β-naphthylamine
AIE — 5-aminoisophthalic acid dimethylester
AFC — 4-trifluoromethyl-coumaryl-7-amine
MCA — 4-methyl-coumaryl-7-amine
*The abbreviated blocking groups are as follows:
Bz — Benzoyl
H—D — Dextrorotatory form of amino acid
Tos — Tosyl
$CH_3$ — Methyl
CBZ — Carbobenzoxy
BOC — Butyloxycarbonyl The 3-layered test device prepared as described herein is used for the quantitative determination of heparin in an unknown plasma sample by first applying the plasma sample to the top, thrombin and AT-III containing, layer of the device. After such contact, any time-related chemical change in the substrate is monitored by reflectance spectrofluorometric or reflectance spectrophotometric means repeatedly over a period of time to obtain at least 2 spectrofluorometric or spectrophotometric values as a function of time and comparing the relationship between the values obtained with values obtained in a like manner using plasma samples containing known amounts of heparin and using such comparison to determine the concentration of heparin in the plasma sample being tested.

The present invention is further illustrated by the following examples. In these examples, TRIS and thrombin (bovine thrombin) were obtained from the Research Products Division of Miles Laboratories, Inc., Whatman 54 paper was from the Whatman Paper Company, the plasma was Thromboscreen ® Universal Coagulation Reference Plasma from Cutter Laboratories, Inc., and S-2238 substrate was from A. B. KABI.

In these examples, reflectance or fluorescence measurements were taken at the optimum wavelength(s) for the indicator (405 nm for S-2238) after applying the plasma dilution to the strips. The percent reflectance values were converted into K/S values by using the following formula:

$$K/S = (1-R)^2/2R$$

where K is the absorption coefficient of the sample, S is the light scattering coefficient of the matrix and R is the fraction of incident light reflected from the reagent strip. This is a simplified version of the Kubelka-Munk equation. The K/S values are related to reflectance measurements.

EXAMPLE I

The substrate pad was prepared by dipping a 3×3 inch piece of Whatman 54 paper through 1 milliliter (ml) of a 5 millimoles (mM) aqueous solution of H-D-phe-pip-arg-pNA (S-2238 thrombin substrate) and drying it in a forced air oven at 35° C. for 30 min. The dried paper was mounted on silvered mylar foil and then on double-sided adhesive and the edges trimmed off. The mounted paper was cut into 1 cm wide strips and mounted ¼ inch from the end of pieces of Trycite polystyrene used for strip handles.

The thrombin/AT-III pad was prepared by dipping a 3×3 inch piece of Whatman 54 paper through 2 ml of a solution containing 0.2 molar (M) Tris-Cl, 0.73M NaCl, 0.3M ethylene diamine tetra acetic acid (EDTA), 200 microliters per milliliter (μl/ml) defibrinogenated plasma (containing AT-III) and 5.6 NIH units/ml of bovine thrombin pH 8.4. The dipping solution components were combined at ice-water bath temperature with the bovine thrombin being added last. Immediately after mixing of the thrombin in the dip solution, the paper was dipped, pulled through scraping bars, and quick frozen by dropping the paper onto a metal tray which was on dry ice. The moisture was removed from the paper by freeze-drying, the edges trimmed from the paper and the paper slit into 1 centimeter (cm) wide strips.

A 1-2 millimeter (mm) wide piece of double-sided adhesive was cut and placed on the back edge of the substrate pad which was already mounted on the Trycite plastic. A 1 cm wide piece of the paper containing thrombin (and plasma AT-III) was placed over the substrate strip and bonded to it by means of the adhesive at its back edge. The edges were trimmed from each plastic piece and the preparation slit into 0.5 cm strips. The strips were stored at 4° C. in a capped bottle containing 3 molecular sieve tablets and used within 1 to 2 days.

Aqueous heparin solutions (Na heparin from procine intestinal mucosa) were prepared containing from 0.01 to 1.0 USP units of heparin/ml. The response of these strips to heparin was tested by adding 30 μl of heparin solution to a strip and monitoring the reflectance change every 10 seconds for 3 minutes in a reflectance photometer using a 400 nm interference filter. The K/S response was linear from 120 seconds to 180 seconds, and the slope was determined by a linear regression of the data in that time. The slope of the regression line d(K/S)/dt plotted against heparin concentration (FIG. 1) shows a definite dose response to heparin. The log-log plot of this relationship (FIG. 2) is reasonably linear.

EXAMPLE II

The chromogenic reagent strips prepared as described in Example I are used with two or more calibrator solutions which contain known amounts of heparin in a matrix similar to blood plasma. Each calibrator is diluted 10-fold in water, and 30 microliter aliquots of the diluted calibrators are applied to the reagent strips and the reflectance of each monitored at 400 nm for 3 minutes subsequent to the sample application. The slopes, d(K/S)dt, of these kinetic curves are calculated by linear regression using the data collected between 90 seconds and 180 seconds. The slopes of the calibrators are plotted versus their known heparin concentrations to create the calibration or standard curve plot which will be used to determine the heparin concentration of plasma samples.

After preparation of the calibration curve, the plasma samples, for which assays of the heparin concentration are desired, are diluted 10-fold in water. Thirty microliter aliquots of each diluted plasma sample are applied to the reagent strips and their reflectance monitored at 400 nm every 5 seconds for 3 minutes. The slope, d(K/S)dt, of each kinetic curve is calculated by a linear regression analysis from the data between 90 and 180 seconds. This slope value is located on the calibration curve and the heparin concentration of the sample read from the opposite axis.

What is claimed is:

1. A method for the preparation of a three layer device for the quantitative determination of heparin in mammalian blood plasma which comprises the steps of:
   (a) providing a first strip of carrier matrix material having incorporated therewith a buffer and a thrombin sensitive fluorogenic or chromogenic substrate, said substrate being capable of interacting with thrombin in such a manner that a time related chemical change detectable by fluorometric or spectrophotometric means takes place when thrombin and the substrate are contacted in a suitable liquid environment;
   (b) contacting a second strip of a carrier matrix material with a fresh, aqueous solution containing a buffer, AT-III and thrombin which solution has been maintained at a temperature below about 20° C. since before addition of the thrombin thereto to saturate the second strip with the solution;
   (c) removing the second strip from the solution, quick freezing it, and eliminating solvent by freeze-drying to provide a second strip containing buffer, AT-III and thrombin;
   (d) attaching the first strip to a strip of water impermeable material; and
   (e) attaching the second strip to the exposed side of the first strip to form a three-layered device suitable for the intended purpose.

2. The method of claim 1 wherein the solution containing AT-III and thrombin is maintained at a temperature of below 5° C.

3. The method of claim 1 wheren the buffer is tris(hydroxymethyl)-aminomethane; N,N-bis-(2-hydroxymethyl)glycine or tris(hydroxymethyl)methyl aminopropanesulfonic acid.

4. The method of claim 1 wherein the substrate is H-D-phe-pip-arg-pNA and the buffer is capable of maintaining the pH in the range of 8.0 to 8.5.

5. The method of claim 1 wherein the ratio of thrombin to AT-III in the aqueous solution is greater than 0.05 NIH unit thrombin:1 $\mu$g AT-III.

6. The method of claim 5 wherein the ratio is from 0.2 NIH unit thrombin:1 $\mu$g AT-III to 0.5 NIH unit thrombin-1 $\mu$g AT-III.

7. The method of claim 1 wherein the carrier matrix of either or both the first strip and second strip is a film or a bibulous material.

8. The method of claim 7 wherein the film is formed of gelatin or agarose.

9. The method of claim 7, the bibulous material is paper, cellulose, wood, a synthetic resin fleece or a woven or nonwoven fabric.

10. A three layer test device suitable for the quantitative determination of heparin in mammalian blood plasma which comprises:
    i. a first upper layer of a carrier matrix material containing a buffer, AT-III and thrombin;
    ii. a second layer adjacent to and in contact with the first layer said second layer comprising a carrier matrix containing a thrombin sensitive fluorogenic or chromogenic substrate and a buffer said substrate being capable of interacting with thrombin in such a manner that a time-related chemical change detectable by fluorometric or spectrophotometric means takes place when thrombin and the substrate are contacted in a suitable liquid environment; and
    iii. a third layer of a water impermeable material beneath the second layer.

11. The test device of claim 10 wherein the substrate is H-D-phe-pip-arg-pNA and the buffer is capable of maintaining the pH in the range of 8.0 to 8.5.

12. The test device of claim 10 wherein the carrier matrix of either or both the first layer and second layer is a film or a bibulous material.

13. The test device of claim 12 wherein the carrier matrix is a film formed of gelatin or agarose.

14. The test device of claim 12 wherein the carrier matrix is a bibulous material selected from paper, cellulose, wood, a synthetic resin fleece or a woven or nonwoven fabric.

15. A method for the quantitative determination of heparin in mammalian blood plasma which comprises:
    (a) contacting mammalian blood plasma with the device described in claim 10;
    (b) monitoring any chemical change in the substrate by reflectance spectrofluorometric or reflectance spectrophotometric means repeatedly over a period of time to obtain at least 2 spectrofluorometric or spectrophotometric values as a function of time; and
    (c) comparing the relationship between the values obtained in step (b) with values obtained in a like-manner using plasma samples containing known amounts of heparin and using such comparison to determine the concentration of heparin in the plasma sample being tested.

* * * * *